United States Patent [19]

Robb

[11] Patent Number: 5,068,056

[45] Date of Patent: Nov. 26, 1991

[54] AQUEOUS DISPERSIONS OF ACICULAR TITANIUM DIOXIDE

[75] Inventor: Jenifer L. Robb, Stockton on Tees, England

[73] Assignee: Tioxide Group PLC, England

[21] Appl. No.: 444,811

[22] Filed: Dec. 1, 1989

[30] Foreign Application Priority Data

Dec. 16, 1988 [GB] United Kingdom ............... 8829402

[51] Int. Cl.$^5$ ............................................. B01J 13/00
[52] U.S. Cl. ............................... 252/313.1; 252/315.4; 106/436; 106/442
[58] Field of Search ........................ 252/313.1, 315.4; 106/436, 442

[56] References Cited

U.S. PATENT DOCUMENTS

| | | | |
|---|---|---|---|
| 3,579,310 | 5/1971 | Lewis et al. | 23/301 |
| 3,728,443 | 4/1973 | Berisford et al. | 423/610 |
| 3,923,968 | 12/1975 | Basque et al. | 423/611 |
| 4,927,464 | 5/1990 | Cowie | 106/436 |

FOREIGN PATENT DOCUMENTS

| | | |
|---|---|---|
| 0073340 | 7/1982 | European Pat. Off. . |
| 0214308 | 3/1987 | European Pat. Off. . |
| 49-450 | 1/1974 | Japan . |
| 52-72833 | 6/1977 | Japan . |
| 53-124627 | 10/1978 | Japan . |
| 54-073193 | 6/1979 | Japan . |
| 55-154317 | 7/1979 | Japan . |
| 57-067681 | 4/1982 | Japan . |
| 58-43912 | 3/1983 | Japan . |
| 58-043912 | 3/1983 | Japan . |
| 58-62106 | 4/1983 | Japan . |
| 59-62517 | 4/1984 | Japan . |
| 59-98009 | 6/1984 | Japan . |
| 59-172415 | 9/1984 | Japan . |
| 59-223231 | 12/1984 | Japan . |
| 61-097133 | 9/1985 | Japan . |
| 60-186418 | 9/1985 | Japan . |
| 61-215216 | 9/1986 | Japan . |
| 1017475 | 1/1966 | United Kingdom . |
| 1185843 | 8/1967 | United Kingdom . |
| 1256341 | 1/1969 | United Kingdom . |
| 1387281 | 3/1975 | United Kingdom . |
| 1541621 | 5/1975 | United Kingdom . |
| 1479988 | 7/1975 | United Kingdom . |
| 1478449 | 6/1977 | United Kingdom . |
| 458535A2 | 7/1979 | United Kingdom . |
| 2206339 | 1/1989 | United Kingdom . |

Primary Examiner—Robert L. Stoll
Assistant Examiner—N. Bhat
Attorney, Agent, or Firm—Banner, Birch, McKie & Beckett

[57] ABSTRACT

An aqueous dispersion of acicular fine particle size titanium dioxide containing from 20 to 60% by weight solids content and a polycarboxylic dispersant is of outstanding use in the preparation of sun screens. The dispersions are transparent to visible light and absorbant to UV light of broad spectrum. Usually the titanium dioxide has a largest dimension within the range 0.01 to 0.15 micron.

The dispersions are produced by milling, preferably in a high speed mill, until the required UV absorbancy is attained.

34 Claims, No Drawings

AQUEOUS DISPERSIONS OF ACICULAR TITANIUM DIOXIDE

This invention relates to dispersions and particularly to aqueous dispersions of titanium dioxide suitable for use in the manufacture of absorbers for UV radiation.

According to the present invention an aqueous dispersion of titanium dioxide comprises water, particles of titanium dioxide having an acicular shape and a dispersing agent being a polycarboxylic acid or a salt thereof and said titanium dioxide being present in an amount to produce a solids content for the dispersion of from 20 to 60 per cent by weight and having a size such that the dispersion is substantially transparent to visible light and has a maximum extinction coefficient (E(max)) in the ultra violet range of wavelengths of at least 30 liters per gm per cm.

According to the present invention an aqueous dispersion of titanium dioxide comprises water, particles of titanium dioxide having an acicular shape and having a ratio of the largest dimension to the shortest dimension within the range 8:1 to 2:1 and wherein the longest dimension is within the range 0.01 to 0.15 microns and a dispersing agent being a polycarboxylic acid or a salt thereof and said titanium dioxide being present in an amount to produce a solids content for the dispersion of from 20 to 60 per cent by weight.

According to the present invention also the preferred aqueous dispersion of the immediately preceding paragraph has a maximum extinction coefficient of at least 30 liters per gram per cm when measured at a wave length of 308 nm.

According to the invention also a method for the manufacture of an aqueous dispersion comprises milling in the presence of particulate grinding medium particulate titanium dioxide in water in the presence of a dispersing agent being a polycarboxylic acid or a salt thereof said titanium dioxide having an acicular shape and is present in an amount sufficient to produce a solids content of from 20 to 60 per cent by weight until the titanium dioxide is dispersed in said water to produce a product absorbant to ultra-violet light and substantially transparent to visible light.

The aqueous dispersions of the present invention contain a high proportion of the specified particulate titanium dioxide and as described there is sufficient present to confer on the dispersion or solids content of at least 20 per cent by weight. The dispersion can have a solids content of up to 60% per cent by weight but preferably sufficient particulate titanium dioxide is present for the aqueous dispersion to have a solids content of from 25 to 50 per cent by weight. The attainment of such high solids contents with the specified particulate titanium dioxide enables the aqueous dispersion to be of beneficial and convenient use in the manufacture of compositions or mixtures to be used to absorb UV radiations. In some cases the aqueous dispersion may be in the form of a light gel which can be mixed easily and reliquefied. This gelling has no adverse effects on the absorption of UV light.

The particulate titanium dioxide is of a specified form. The material is acicular in shape and preferably the particles have a ratio of the largest dimension to the shortest dimension within the range 8:1 to 2:1.

Usually the particles of titanium dioxide have a largest dimension within the range 0.01 to 0.15 micron and preferably 0.02 to 0.1 micron. Preferably the particulate material has a narrow size range with at least 80% by weight falling within the range of largest dimensions of 0.01 to 0.15 micron.

The particles of titanium dioxide forming the aqueous dispersions of the invention can be anatase, rutile or amorphous titanium dioxide and each particle can be composed of aggregated smaller particles or crystals but preferably each particle is a single particle of the desired size.

The particles of titanium dioxide can be uncoated or coated with one or more hydrous oxides of a metal such as aluminum, zirconium, zinc or titanium and of silicon. Preferably however when the particles are coated then the coating includes a hydrous oxide of aluminium and of silicon, e.g. in a weight ratio of $Al_2O_3:SiO_2$ of at least 1.5 and not greater than 4.5. Preferably the weight ratio $Al_2O_3:SiO_2$ in the coating is from 2.0 to 3.5.

Usually the actual amount of the coating is such that the amount of hydrous oxide when expressed as the oxide, e.g. $Al_2O_3$, is from 1.0 to 30.0 weight percent based on weight of titanium dioxide and preferably from 5.0 to 20.0 weight per cent oxide, e.g. $Al_2O_3$, on weight of titanium dioxide. When the particles are coated with a hydrous oxide of aluminum and of silicon then the amount of hydrous oxide of silicon will be that necessary to maintain the ratio of the amounts of coating hydrous oxides, $Al_2O_3$ and $SiO_2$, within the specified range and generally speaking the weight of the hydrous oxide of silicon will be within the range 0.2 to 20.0 weight percent as $SiO_2$ based on titanium dioxide and preferably from 1.5 to 7.0 weight percent.

The particulate material of the present invention may be formed by any suitable process for making acicular products. Typical processes may involve hydrolysis of an appropriate titanium compound such as titanium tetrachloride or an organic or inorganic titanate or oxidation of an oxidisable titanium compound for example in the vapour state.

A typical process involves the preparation of a solution of a soluble titanium salt which is then hydrolysed to form hydrous titanium oxide. The solution can be that obtained in the so-called "sulphate" process for the manufacture of titanium dioxide pigment in which a titaniferous ore is digested with concentrated sulphuric acid and the digestion cake dissolved in water or dilute acid to produce a solution of titanyl sulphate. During the process additional process stages of classification and reduction are usually employed. Hydrolysis of the titanyl sulphate solution produces the precipitate of hydrous titania which is sometimes called "pulp". Soluble iron compounds remain in solution and after neutralisation and washing to an appropriate degree of impurity level the precipitated pulp of hydrous titania is treated with, say sodium hydroxide and subsequently hydrochloric acid to produce the acicular titanium dioxide.

Usually prior to coating of the acicular titanium dioxide product it is preferred to mill the product to an appropriate particle size falling within that specified hereinbefore. Milling conveniently can be effected in a wet milling process employing a grinding medium such as sand which can be separated easily and effectively from the milled pulp. Milling, preferably, as carried out in the presence of a dispersing agent which may be an alkali metal silicate, e.g. sodium silicate, which provides at least some of the source of the coating hydrous silica when this is to be deposited subsequently. Should another dispersant be used for example, an organic dispersant, then the source of coating hydrous silica is added subsequently if to be present.

If desired the milled product is then treated to deposit the coating of the hydrous oxide(s) in the specified amounts. To an aqueous dispersion of the particulate product containing a hydrolysable salt or salts of the desired metal and/or of silicon there is added a reagent which effects hydrolysis of the salt to form the chosen hydrous oxide(s). Typically aluminium sulphate can be a source of alumina or an alkaline aluminate can be employed or if desired both an acidic aluminium salt and an alkaline solution of an aluminate can be added either together or sequentially. Other metal salts and silicates can be used depending on the particular desired coating.

Depending on the pH of the dispersion of the product, hydrolysis and precipitation may require the addition of an alkali or an acid as the reagent. The preferred coating is obtained by adding to an acid reacting dispersion of the particles of titanium dioxide containing an alkali metal silicate an amount of aluminium sulphate followed by an amount of an alkali metal aluminate prior to the addition of a mineral acid such as sulphuric acid to effect formation and precipitation of hydrous alumina and adjustment of the pH of the dispersion to a value in the range 6 to 8, preferably pH 6.8 to 7.5.

The product can be separated from the aqueous dispersion, washed and then dried at an elevated temperature of say 70° C. to 110° C. or even higher. In contrast to the usual "sulphate" process for the production of pigmentary titanium dioxide no calcination of hydrous titania is carried out prior to coating. Consequently it may be that some of the titania in the product of the invention, if prepared from pulp, is present in a hydrous form even after drying.

Alternatively the particles of titania according to the present invention can be prepared by decomposition or hydrolysis of suitable titanium compounds e.g. titanium tetrachloride. Typically high temperature hydrolysis of an organic titanium compound such as a titanium alkoxide can be used to produce a fine particle sized titania pulp to be converted to acicular form. Oxidation or hydrolysis in the vapour state of titanium halides under appropriate conditions can be also used to prepare the titania to be coated.

The products of the present invention have the property of absorbing UV light and transmitting visible light. This means that the products can find use in a wide variety of applications wherein it is important to maintain transparency of visible light while substantially preventing transmission of UV light to a surface. Cosmetics, in any form such as lotions, creams, milks, pastes, sticks, face powders, sun screens and hair care products are a number of applications for the products of the invention.

The dispersions of the present invention are prepared by milling the particulate titanium dioxide into water in the presence of a specified organic dispersing agent.

The mill which is employed to effect the grinding of the titanium dioxide product in the water is one which uses a particulate grinding medium to grind the product. Such mills are the various types of mills equipped with one or more agitators and using sand or glass beads or ceramic beads or other particles as the particulate grinding medium. Particularly useful are those mills which operate at a high speed and depending on the size of mill a speed of the order of 2500 rev. per minute (r.p.m) is not unusual. For instance mills operating at a speed of from 500 r.p.m to 6000 r.p.m are suitable. Agitator mills in which the tip speed of the agitator is up to and can exceed 10 metres/sec are of use. If desired the mill can be cooled. Also the dispersions can be pre-mixed using a high speed stirrer or the water can be added to the mill initially and then the titanium dioxide and the organic dispersant co-added to the water subsequently. After milling has been carried out for the required time the dispersion is separated from the grinding medium.

The dispersing agent which is present in the aqueous dispersion of the present invention is a polycarboxylic acid or a salt thereof. Partially or fully neutralized salts are usable e.g. the alkali metal salts and ammonium salts. Examples of dispersing agents are polyacrylic acids, substituted acrylic acid polymers, acrylic copolymers, sodium and/or ammonium salts of polyacrylic acids and sodium and/or ammonium salts of acrylic copolymers. Such dispersing agents are typified by polyacrylic acid itself and sodium or ammonium salts thereof as well as copolymers of an acrylic acid with other suitable monomers such as a sulphonic acid derivative such as 2-acrylamido 2-methyl propane sulphonic acid. Comonomers polymerisable with the acrylic or a substituted acrylic acid can also be one containing a carboxyl grouping. Usually the dispersing agents have a molecular weight of from 1000 to 10,000 and are substantially linear molecules.

The amount of the dispersion agent used is usually within the range 5 to 35 per cent by weight of the titanium dioxide in the dispersion and preferably 10 to 25 per cent by weight.

The preferred dispersions of the present invention have a maximum extinction coefficient of at least 30 liters per gram per cm at a wavelength of 308 nm. More preferably the dispersion has a maximum extinction coefficient of at least 40 liters per gram per cm at a wavelength of 308 nm. The products of the invention are substantially transparent to visible light.

In the past an ideal sunscreen was considered as being one which absorbs or filters out UVB radiation (290–320 nm), as it is this which causes erythema. More recently, however, there has been growing concern about the effect that UVA radiation (320–400 nm) has on the skin.

It is now widely accepted that the defintion of the ideal sunscreen is one which can provide photoprotection from both UVB and UVA radiation. This ideal sunscreen must therefore contain agents which can absorb or filter out radiation in the range 290–400 nm.

The spectra of the acicular ultra-fine titanium dioxide dispersions 40% solid content of the invention indicate that there should be protection provided in both the UVB and UVA regions, and values of extinction coefficients covering the range 290–400 nm are given as shown below.

| EXAMPLE NO. | 3 | 5 | 25 | 19 | ANATASE TITANIUM DIOXIDE PIGMENT |
|---|---|---|---|---|---|
| E (300 nm) | 47.8 | 56.9 | 57.2 | 49.6 | 18.9 |
| E (320 nm) | 37.2 | 39.2 | 44.2 | 41.6 | 19.2 |
| E (340 nm) | 26.1 | 27.5 | 29.2 | 29.0 | 20.1 |
| E (360 nm) | 18.3 | 21.0 | 18.7 | 19.5 | 21.3 |
| E (380 nm) | 13.9 | 15.7 | 13.1 | 13.8 | 21.9 |
| E (400 nm) | 10.6 | 12.7 | 9.3 | 10.2 | 22.3 |

For comparison, extinction coefficients are given for similar dispersions of anatase titanium dioxide pigment (uncoated) of solids contents of 40% by weight. It can be seen that extinction coefficients in the UVB region (290–320 nm) are much lower for pigmentary $TiO_2$ than for the products of the invention.

In the UVA region, again extinction is higher for the acicular ultra-fine grade between 320–340 nm. From 360 nm to 400 nm the pigmentary $TiO_2$ has a higher extinction coefficient, but this level of extinction is maintained into the visible region for the pigmentary grade. This means that the pigment dispersion looks white when applied to the skin.

The ultra-fine $TiO_2$ extinction is very low in the visible region (above 400 nm) which means that the dispersion is more transparent and aesthetically acceptable than the pigment dispersion, while still maintaining good UVB and UVA extinction coefficients.

The invention is illustrated in the following Examples.

EXAMPLE 1

Ilmenite was digested with concentrated sulphuric acid. The digestion cake obtained was dissolved in water to form a crude liquor containing iron and titanium sulphates and some suspended insoluble matter. Any iron present in the ferric form was reduced chemically prior to filtering insoluble matter. The liquor after any necessary crystallisation and filtration was concentrated by vacuum treatment and then hydrolysed to precipitate hydrous titanium dioxide by boiling and addition of any necessary reaction agent. The product on filtering was a pulp of uncoated hydrous $TiO_2$.

In the subsequent process any water added or used was taken to be demineralised water.

The pulp of the uncoated hydrous $TiO_2$ obtained was diluted to a concentration of 280 grams per liter $TiO_2$ and a sample amount of 2.5 liters taken and heated to 60° C. Aqueous sodium hydroxide solution containing 700 grams per liter NaOH in an amount of 1.5 liters was heated to 90° C. and then transferred to a reaction flask having a volume of 5 liters fitted with a condenser. The hot diluted pulp was added over a period of 30 minutes to the reaction flask whilst agitating the contents vigorously and the mixture temperature was held at 117° C. whilst agitating for a period of 2 hours after the addition had been completed. Cold water was added to quench the solution in the flask to 90° C. and to decrease the concentration of titanium dioxide to 140 grams per liter. The amount of water added was approximately 20% of the total volume achieved. The contents were agitated for a further 15 minutes at this temperature of 90° C. prior to cooling to a temperature of 50° to 55° C. by the addition of a further amount of cold water which reduced the concentration of titanium dioxide to about 80 to 90 grams per liter. The dispersion was filtered and the filter cake washed with warm water at a temperature of 50° C. to 60° C. so that the filtrate contained less than 1500 ppm $Na_2O$. The washed filter cake was then reslurried in water to a concentration of 200 grams per liter $TiO_2$ and at this stage the product was sodium titanate.

Two liters of the washed sodium titanate was added to a reaction flask having a volume of 6 liters and fitted with a condenser. The pH of the dispersion in the flask was reduced to a value within the range 2.8 to 3.1 by the addition of aqueous hydrochloric acid (30% w/w) and the mixture then heated to a temperature of 60° C. at the rate of 1° C. per minute. The pH of the mixture was rechecked and adjusted, if necessary, to a value within the range 2.8 to 3.1 by a further addition of the aqueous hydrochloric acid. The dispersion was held at this temperature for 30 minutes whilst agitated. A further quantity of hydrochloric acid was then added such that the volume added was 0.754 liters of 30% HCl acid per kilogram of $TiO_2$ in the dispersion such that the ratio of $HCl/TiO_2$ equalled 0.26. The slurry was then heated to the boiling point over a period of 40 minutes and held at the boiling point for a period of 90 minutes whilst being agitated. The treated product was then quenched by addition of two liters of water and the dispersion had a pH value of 0.4. Sodium hydroxide solution at a concentration of 400 grams per liters NaOH was then added to neutralise the dispersion to a pH of 7.5 and approximately 460 ml of the aqueous sodium hydroxide was required. The dispersion was filtered and the filter cake washed with two liters of water. The washed filter cake was then redispersed with a further quantity of two liters of water and filtered again to produce a filter cake having a solids content of 34% by weight.

The filter cake is then dried in an oven at 110° C. overnight. The product was acicular rutile titanium dioxide having an average size of $0.02 \times 0.1$ microns.

276 g of the dried $TiO_2$ product was added to 414 g of water and 33.1 g of sodium polyacrylate obtainable under the name Antiprex A. This mixture was milled in a sandmill for 1 hour using 800 ml of glass beads, known as Ballotini (Grade 4), as grinding media to disperse the product in water and to separate any aggregated particles. The glass beads were removed from the milled dispersion at the end of the milling period by filtration.

The millbase, which contained 38.2% solids was diluted with demineralised water in the proportion 0.1 g millbase in 100 ml water, and then 1 ml of this diluted millbase in 20 ml water. The mill base was then exposed in a spectrometer (Beckman DU-50) with a 1 cm pathlength and the absorbance of UV and visible light measured.

Extinction coefficients at two wavelength and at the maximum wavelength were then calculated from the equation $A = E.c.1$ where $A$ = absorbance, $E$ = Extinction coefficient in liters per gram per cm, $c$ = concentration in grams per liter and $1$ = pathlength in cm. $W$ = wavelength (nm).

Results were:
E(524 nm) 5.1
E(308 nm) 60.8
E(max) 65.5
W(max) 293

EXAMPLE 2

As Example 1 except that milling was carried out on a high speed bead mill (Eiger M750-SSE-EXD) using 400 ml glass Ballotini as grinding media. 385 g $TiO_2$ was mixed with 658 g of water and 46.4 g of the sodium polyacrylate used in Example 1. The dispersion was milled for 30 mins and the solids content of the dispersion was 35.4%.

After separation from the grinding aid a 0.1 g portion was diluted as previously with water and this diluted sample was exposed in a spectrometer (Beckman DU-50). Extinction coefficients were calculated as previously.

E(524 nm) 5.5
E(308 nm) 45.5
E(max) 50.7
W(max) 279

EXAMPLE 3

The procedure of Example 1 was repeated to obtain a washed filter cake of 34% by weight solids content of uncoated titanium dioxide.

882 grams of the filter cake (300 grams $TiO_2$) was diluted to a concentration of 100 grams per liter $TiO_2$ with demineralised water and mixed with sodium silicate in an amount equivalent to 5% by weight $SiO_2$ on weight of $TiO_2$ and milled in a sand mill for 2 hours after adjusting the pH of the dispersion to 10.0 to 11.5 with aqueous sodium hydroxide. The grinding medium was Ottowa sand and was removed from the milled dispersion at the end of the milling period by filtration.

The aqueous dispersion after removal of the sand had a pH of 9.1 and was heated to 60° C. and maintained at this during the coating operation.

To the stirred dispersion aqueous aluminium sulphate solution (68 grams per liter $Al_2O_3$ equivalent) was added dropwise in an amount sufficient to introduce aluminium sulphate in an amount equivalent to 5% $Al_2O_3$ on weight of $TiO_2$ over a period of 60 minutes. Approximately 219 mls of the solution were added. After the addition has been completed the dispersion had a pH of 2.4 and was allowed to age for 30 minutes at 60° C. whilst stirring was maintained.

An alkaline solution of sodium aluminate (80 grams per liter $Al_2O_3$) was then added over a period of 60 minutes to the stirred dispersion in an amount sufficient to introduce the equivalent of 10% by weight $Al_2O_3$ on weight of $TiO_2$. Approximately 375 mls of the solution was found to have been added. The dispersion which had a pH of 11.8 was stirred at 60° C. for 45 minutes.

Sulphuric acid (10%) was added to the aqueous dispersion to reduced the pH to 7.5. The neutralised dispersion was aged for 15 minutes whilst being stirred. The dispersion was filtered to produce a filter cake of the coated product which was then washed with 1 liter of demineralised water. The cake was redispersed in 1 liter of demineralised water, re-filtered and then washed again with demineralised water.

The product was dried at 110° C. overnight. The product was acicular rutile titanium dioxide having an average size of 0.02×0.10 microns with a coating of hydrous silica in an amount equivalent to 4.8% by weight $SiO_2$ on $TiO_2$ and hydrous alumina in an amount of 11.2% by weight $Al_2O_3$ on $TiO_2$ as determined by analysis of the product.

50 g of the dried coated $TiO_2$ product was added to 70 ml of water and 5.03 g of the sodium polyacrylate used in Example 1. This mixture was milled in a high speed bead mill (Eiger M-50-VSE) for 2 hours using 35 ml of glass beads. The millbase, which contained 40% solids was diluted as in previous examples and exposed in a spectrometer. Extinction coefficients are listed below:

E(524 nm) 4.2
E(308 nm) 44.5
E(max) 50.0
W(max) 287 nm

EXAMPLE 4

276 g of the dried coated $TiO_2$ product of Example 3 was added to 414 g of water and 33.1 g of the sodium polyacrylate used in Example 1. The mixture was milled in a sandmill for 1 hour using 800 g of glass beads. The millbase, which contained 38% solids, was diluted as previously and a spectrum was recorded E(525 nm) 5.6
E(308 nm) 49.7
E(max) 53.1
W(max) 288

EXAMPLE 5

A solution of titanium tetrachloride in hydrochloric acid having an acid/titanium ratio (weight ratio) of 1.77 was prepared containing 200 grams per liter $TiO_2$ equivalent. An aqueous solution of sodium hydroxide (110 grams per liter) was prepared from carbonate free ingredients.

To a 3 liter glass flask fitted with a stirrer there was added 1203 ml of the aqueous sodium hydroxide solution and 400 ml of water (demineralised). To the stirred solution there was then added 400 mls of the titanium tetrachloride solution over a period of 15 minutes and during this period the stirrer speed was controlled at 100 rev. per minute. After the addition had been completed the temperature was raised from its initial value of 40°-45° C. to 82° C. at a rate of 1° C. per minute and the mixture was held at this temperature for a further 120 minutes whilst stirring continued. During the heating to the temperature of 82° C. the solution was observed to clear partially, normally at about 60°-70° C. as the titanium dioxide peptises and then re-precipitates.

After holding at 82° C. for 120 minutes the mixture was added to 2.5 liters of cold distilled water to quench the mixture then a further 5 liters of the water at 60° C. is added to the quenched mixture. Sodium hydroxide solution (110 grams per liter) is then added to the mixture to neutralise the mixture to a pH value of 7.5. The neutralised and flocculated mixture was allowed to settle, filtered and the cake washed with 2.5 liters of water by stirring prior to refiltering. The cake was washed again by re-slurrying with 2.5 liters of water and filtered to produce a cake having a solids content of 22% by weight.

The titanium dioxide in the cake was acicular and rutile having an average size of 0.01 to 0.05 microns.

The acicular titanium dioxide product obtained was coated in accordance with Example 3 with hydrous silica (5% by weight on weight of $TiO_2$) and hydrous alumina (15% by weight).

276 g of the $TiO_2$ product was added to 414 g of water and 33.1 g of the sodium polyacrylate used in Example 1. This mixture was milled in a sandmill for 1 hour using 800 g of glass beads. The millbase, which contained 41% solids, after milling, was diluted as previously and a spectrum was recorded.

E(524 nm) 4.9
E(308 nm) 35.7
E(max) 42.7
W(max) 276 nm

EXAMPLE 6

Ilmenite was digested with concentrated sulphuric acid. The digestion cake obtained was dissolved in water to form a crude liquor containing iron and titanium sulphate and some suspended insoluble matter. Any iron present in the ferric form was reduced chemically prior to filtering insoluble matter. The liquor after any necessary crystallisation and filtration was concentrated by vacuum by treatment and then hydrolysed to precipitate hydrous titanium dioxide by boiling and addition of any necessary reaction agent. The product on filtering was a pulp of uncoated hydrous $TiO_2$.

Four kilograms of the pulp so obtained was mixed with 5 liters of demineralised water. The pH of the diluted pulp was 1.9 and 375 ml of an aqueous solution of sodium hydroxide (containing 400 grams per liter NaOH) added to increase the pH to a value within the range 7.5 to 7.8. The dispersed pulp was filtered and the cake washed with 6.5 liters of demineralised water. The washed filter cake was then redispersed in 3 liters of demineralised water and the pH measured at a value of 8.4. Sulphuric acid (10%) (118 ml) was added to reduce the pH of the dispersion to 7.5 prior to filtering again. After washing the filter cake with 6.0 liters of demineralised water the solids content of the cake was 44.3% by weight.

The filter cake was dried in an oven at 110° C. overnight. 50 g of the product was added to 70 g of water and 8.78 g of the sodium polyacrylate used in Example A. The mixture was milled (Eiger M-50-VSE) for 2 hours using 35 ml glass beads.

The millbase which contained 38.8% solids was diluted and a spectrum was recorded.

E(524 nm) 5.6
E(308 nm) 40.4
E(max) 54.1
W(max) 257 nm

EXAMPLE 7

276 g of the dried $TiO_2$ product of Example 1 was added to 257 g of water and 33.1 g of the sodium polyacrylate used in Example 1. This mixture was milled in a sand mill for 1 hour using 800 ml of glass beads. The millbase, which contained 48.7% solids was diluted as before and a spectrum was recorded.

E(524 nm) 6.9
E(308 nm) 44.3
E(max) 47.6
W(max) 293

EXAMPLE 8

35 g of the dried coated $TiO_2$ product of Example 3 was added to 61.5 g of water and 3.5 g of a dispersant which is a sodium salt of an acrylic copolymer (35% solution) obtainable under the name Bevaloid 226/35. The mixture was milled in a sand mill for 1 hour using 50 g of glass beads. The millbase, which contained 35% solids was diluted as previously and a spectrum was recorded.

E(524 nm) 3.3
E(308 nm) 43.1
E(max) 45.1
W(max) 296

EXAMPLE 9

35 g of the same dried coated $TiO_2$ product used in Example 8 was added to 61.5 g of water and 3.5 g of a sodium salt of an acrylic acid (50% solution) obtainable under the name Bevaloid 6770. The mixture was milled in a sand mill for 1 hour using 50 g of glass beads. The millbase, which contained 35% solids, was diluted as previously and a spectrum was recorded.

E(524 nm) 4.9
E(308 nm) 46.4
E(max) 49.0
W(max) 296 nm

EXAMPLE 10

35 g of the same dried coated $TiO_2$ product used in Example 8 was added to 61.5 g of water and 3.5 g of a polyacrylic acid of molecular weight 2100 and obtainable under the Carbopol 420. The mixture was milled as in Example 9. Millbase was 35% solids.

E(524 nm) 6.6
E(308 nm) 41.6
E(max) 42.9
W(max) 296

EXAMPLE 11

35 g of the same dried coated $TiO_2$ product used in Example 8 was added to 61.5 g of water and 3.5 g of a polyacrylic acid having a molecular weight of 5100 and obtainable under the name Carbopol 430. Mixture milled as in Example 9. The millbase which contained 35% solids was diluted as before.

E(524 nm) 4.9
E(308 nm) 46.5
E(max) 48.2
W(max) 296

EXAMPLE 12

328 g of the same dried coated $TiO_2$ product used in Example 8 was added to 369.2 g of water and 32.8 g of a fully neutralised sodium salt of a polycarboxylic acid obtainable under the name DP6. The sample was milled in a sandmill for 1 hour using 800 g of glass beads. The millbase, which contained 42.8% solids after milling, was diluted as before.

E(524 nm) 4.8
E(308 nm) 51.4
E(max) 57.1
W(max) 293

EXAMPLE 13

385 g of the acicular titanium dioxide product produced by the method of Example 5 was used, except that it was uncoated. This product was mixed with 658 g of water and 46.4 g of the sodium salt used in Example 12 obtainable under the name DP6, and was milled for 30 minutes on a high speed beadmill (Eiger M750-SSE-EXD). The solids content of the dispersion was 35.4% and this was diluted as previously and a spectrum was recorded (Perkin Elmer Lambda 2 UV/Vis Spectrometer).

E(524 nm) 2.5
E(308 nm) 28.4
E(max) 35.8
W(max) 279 nm

EXAMPLE 14

50 g of the acicular titanium dioxide product in Example 1 was added to 58.8 g of water and 4.31 g of an ammonium salt of an acrylic acid obtainable under the name Dispex A40. The product was milled (Eiger M50VSE) for 2 hours using 35 ml of glass beads. The millbase, which had a solids content of 44.2% was diluted as before and a spectrum was recorded.

E(524 nm) 5.0
E(308 nm) 44.6
E(max) 46.7
W(max) 294 nm

EXAMPLE 15

50 g of the acicular product produced in Example 1 was added to 58.8 g of water and 3.01 g of the fully neutralized sodium salt used in Example 12. The sample was milled as in Example 14. The millbase, which had a solids content of 44.7% was diluted as before and a spectrum was recorded.
E(524 nm) 3.2
E(308 nm) 55.5
E(max) 61.4
W(max) 290 nm

EXAMPLE 16

50 g of the acicular titanium dioxide product of Example 8 was added to 58.8 g of water and 5.84 g of a sodium salt of a polymethacrylic acid having a molecular weight of 12000 and obtainable under the name Orotan 850. The sample was milled as in Example 14. The millbase, which had a solids content of 43.6% was diluted as before.
E(524 nm) 7.3
E(308 nm) 45.4
E(max) 46.4
W(max) 298 nm

EXAMPLE 17

50 g of the acicular titanium dioxide product of Example 8 was added to 58.8 g of water and 6.5 g of the ammonium salt of an acrylic acid as used in Example 14. The sample was milled as in Example 14. The millbase, which contained 43.4% solids, was diluted as before.
E(524 nm) 6.1
E(308 nm) 50.5
E(max) 52.7
W(max) 294 nm

EXAMPLE 18

385 g of the acicular titanium dioxide product of Example 5 was mixed with 658 g water and 45.3 g of the sodium salt used in Example 16. This mixture was milled for 45 minutes (Eiger M750-SSE-EXD). The solids content of the dispersion was 35.4% and this was diluted as before.
E(524 nm) 3.6
E(308 nm) 30.1
E(max) 37.2
W(max) 278 nm

EXAMPLE 19

The titanium dioxide product was as Example 3, except that the product was not dried at 110° C. overnight—instead the $TiO_2$ filtercake was used after washing. The % solids in this filtercake was 23.6%. 600 g of this pulp was additioned with 14.2 g of the sodium polyacrylate used in Example 3 and this mixture was milled for 1 hour on a sandmill. The millbase, which contained 23.1% solids was diluted as previously.

E(524 nm) 3.4
E(308 nm) 47.3
E(max) 50.0
W(max) 293 nm

EXAMPLE 20

The 40% $TiO_2$ aqueous dispersion from Example 3 was incorporated into the oil in water sunscreen formulation given below, and a range of sunscreens containing 0, 2.5, 5.0, 7.5% $TiO_2$ were prepared by adding varying amounts of the $TiO_2$ dispersion. The sunscreens were made by heating phase A to 75° C. Heat phase B to 75° C. and add to phase A, mixing with a Silverson stirrer. Phase C is then added. The batch is cooled to 40° C. and then phases D and E are added.

The sunscreen formulations are as follows:

| | | % BY WEIGHT OF INGREDIENTS | | |
|---|---|---|---|---|
| PHASE | INGREDIENT | 0% $TiO_2$ | 2.5% $TiO_2$ | 5.0% $TiO_2$ |
| A | Deionised water | 62.95 | 56.70 | 50.45 |
| A | Thickener (Carbopol 940) (2% Solution) | 15.00 | 15.00 | 15.00 |
| A | Tetrasodium EDTA | 0.10 | 0.10 | 0.10 |
| A | Propylene Glycol | 2.00 | 2.00 | 2.00 |
| B | Mineral oil 65/75 | 7.50 | 7.50 | 7.50 |
| B | Isopropyl myristate | 5.00 | 5.00 | 5.00 |
| B | Stearic Acid XXX | 3.00 | 3.00 | 3.00 |
| B | Emulsifier (Promulgen D) | 1.50 | 1.50 | 1.50 |
| B | Silicone oil (SF96-100) | 2.00 | 2.00 | 2.00 |
| C | Triethanolamine 99% | 0.75 | 0.75 | 0.75 |
| D | Preservative (Glydant) | 0.20 | 0.20 | 0.20 |
| E | $TiO_2$ Dispersion (40%) | 0.00 | 6.25 | 12.50 |

Similarly, for the 7.5% $TiO_2$ sunscreen, 44.20% dionised water was used and 18.75% of the 40% $TiO_2$ aqueous dispersion.

(EDTA = ethylenediamine tetra acetic acid).

These sunscreens were tested for monochromatic protection factors and the Sun Protection Factors (SPF) of the sunscreens were calculated using the in vitro method described by Dr. B. L. Diffey and J. Robson in the Journal of the Society of Cosmetic Chemists, 40, 1989.

This method involves obtaining monochromatic protection factors every 5 nm over a range of wavelengths from 290–400 nm, and from these the sun protection factor can be calculated. The suncreams were applied at 2 ul/cm² (ul = microlitres).

The monochromatic protection factors can assist in predicting if the product will be efficient as a UVB absorber, a UVA absorber or indeed as both a UVB and UVA absorber. The following results were obtained.

| EXAMPLE 20, 0% $TiO_2$ | | EXAMPLE 20, 2.5% $TiO_2$ | | EXAMPLE 20, 5% $TiO_2$ | | EXAMPLE 20, 7.5% $TiO_2$ | |
|---|---|---|---|---|---|---|---|
| Wavelength nm | Monochromatic Protection Factor | Wavelength nm | Monochromatic Protection Factor | Wavelength nm | Monochromatic Protection Factor | Wavelength nm | Monochromatic Protection Factor |
| 290 | 1.5 ± .1 | 290 | 5.0 ± .9 | 290 | 7.8 ± 1.7 | 290 | 11.5 ± 1.8 |
| 295 | 1.4 ± .1 | 295 | 4.8 ± .8 | 295 | 7.7 ± 1.6 | 295 | 11.3 ± 1.8 |
| 300 | 1.4 ± .2 | 300 | 4.7 ± .7 | 300 | 7.6 ± 1.5 | 300 | 11.3 ± 1.9 |
| 305 | 1.4 ± .1 | 305 | 4.6 ± .7 | 305 | 7.6 ± 1.4 | 305 | 11.2 ± 1.8 |
| 310 | 1.4 ± .1 | 310 | 4.5 ± .6 | 310 | 7.4 ± 1.3 | 310 | 11.1 ± 1.8 |
| 315 | 1.4 ± .1 | 315 | 4.2 ± .6 | 315 | 7.1 ± 1.1 | 315 | 10.6 ± 1.7 |
| 320 | 1.4 ± .1 | 320 | 4.0 ± .5 | 320 | 6.8 ± 1.0 | 320 | 10.2 ± 1.6 |
| 325 | 1.4 ± .1 | 325 | 3.7 ± .4 | 325 | 6.4 ± .8 | 325 | 9.8 ± 1.5 |
| 330 | 1.4 ± .1 | 330 | 3.5 ± .4 | 330 | 5.9 ± .7 | 330 | 9.1 ± 1.5 |
| 335 | 1.3 ± .1 | 335 | 3.2 ± .3 | 335 | 5.4 ± .6 | 335 | 8.4 ± 1.4 |
| 340 | 1.3 ± .1 | 340 | 2.9 ± .3 | 340 | 5.0 ± .6 | 340 | 7.7 ± 1.4 |
| 345 | 1.3 ± .1 | 345 | 2.7 ± .2 | 345 | 4.5 ± .5 | 345 | 7.1 ± 1.3 |
| 350 | 1.2 ± .1 | 350 | 2.4 ± .2 | 350 | 4.1 ± .5 | 350 | 6.4 ± 1.2 |

-continued

| EXAMPLE 20, 0% TiO$_2$ | | EXAMPLE 20, 2.5% TiO$_2$ | | EXAMPLE 20, 5% TiO$_2$ | | EXAMPLE 20, 7.5% TiO$_2$ | |
|---|---|---|---|---|---|---|---|
| Wavelength nm | Monochromatic Protection Factor | Wavelength nm | Monochromatic Protection Factor | Wavelength nm | Monochromatic Protection Factor | Wavelength nm | Monochromatic Protection Factor |
| 355 | 1.2 ± .1 | 355 | 2.3 ± .1 | 355 | 3.8 ± .4 | 355 | 5.8 ± 1.1 |
| 360 | 1.2 ± .1 | 360 | 2.1 ± .1 | 360 | 3.5 ± .4 | 360 | 5.3 ± 1.0 |
| 365 | 1.2 ± .1 | 365 | 2.0 ± .1 | 365 | 3.2 ± .4 | 365 | 4.8 ± .9 |
| 370 | 1.2 ± .1 | 370 | 1.9 ± .1 | 370 | 3.0 ± .4 | 370 | 4.4 ± .8 |
| 375 | 1.2 ± .1 | 375 | 1.9 ± .1 | 375 | 2.8 ± .3 | 375 | 3.9 ± .7 |
| 380 | 1.2 ± .1 | 380 | 1.8 ± .1 | 380 | 2.6 ± .3 | 380 | 3.6 ± .6 |
| 385 | 1.2 ± .1 | 385 | 1.7 ± .1 | 385 | 2.4 ± .3 | 385 | 3.2 ± .5 |
| 390 | 1.2 ± .1 | 390 | 1.6 ± .1 | 390 | 2.3 ± .3 | 390 | 3.0 ± .4 |
| 395 | 1.2 ± .1 | 395 | 1.6 ± .1 | 395 | 2.2 ± .2 | 395 | 2.8 ± .4 |
| 400 | 1.2 ± .1 | 400 | 1.6 ± .1 | 400 | 2.2 ± .2 | 400 | 2.6 ± .4 |

The overall SPF values obtained were as follows:

| % TiO$_2$ | SPF |
|---|---|
| 0.0 | 1.4 ± 0.1 |
| 2.5 | 4.1 ± 0.2 |
| 5.0 | 6.7 ± 0.5 |
| 7.5 | 10.0 ± 0.6 |

These overall SPF values in this Example and those following are obtained from CIE (1987) action spectrum and solar spectrum at 40 degrees N and solar altitude of 20 degrees.

The results for the monochromatic protection factors show that there is protection provided throughout the UVB and UVA region.

EXAMPLE 21

The 40% TiO$_2$ aqueous dispersion from example 3 was incorporated into the water in oil sunscreen formulation given below and two sunscreens were formulated, containing 2.5% and 10% TiO$_2$.

The sunscreams were made as follows:
Add items 3 and 4 to water with mixing. Slowly add TiO$_2$ dispersion and heat with agitation to 75° C. Add phase A to phase B at 75° C. with vigorous agitation. Cool with mixing to room temperature.

The suncream formulations are:

| No. | PHASE | INGREDIENT | % BY WEIGHT OF INGREDIENT | |
|---|---|---|---|---|
| | | | 2.5% TiO$_2$ | 10.0% TiO$_2$ |
| 1 | A | TiO$_2$ Dispersion (40%) | 6.25 | 24.00 |
| 2 | A | Deionised water | 54.45 | 35.70 |
| 3 | A | Propylene glycol | 3.00 | 3.00 |
| 4 | A | Preservative (Glydant) | 0.20 | 0.20 |
| 5 | B | Octyl palmitate | 11.00 | 11.00 |
| 6 | B | Mineral oil 65/75 | 7.50 | 7.50 |
| 7 | B | Emulsifier (Elfacos E 200) | 5.00 | 5.00 |
| 8 | B | Stabiliser (Elfacos ST 9) | 8.60 | 8.60 |
| 9 | B | Emollient (Elfacos C 26) | 4.00 | 4.00 |

These sunscreams were tested for monochromatic protection factors and SPF using the method above and the following results were obtained

| EXAMPLE 21, 10% TiO$_2$ | | EXAMPLE 21, 2.5% TiO$_2$ | |
|---|---|---|---|
| Wavelength nm | Monochromatic Protection Factor | Wavelength nm | Monochromatic Protection Factor |
| 290 | 25.0 ± 5.6 | 290 | 9.5 ± 1.7 |
| 295 | 25.7 ± 5.7 | 295 | 9.5 ± 1.8 |
| 300 | 25.8 ± 5.8 | 300 | 9.4 ± 1.8 |
| 305 | 25.8 ± 6.1 | 305 | 9.3 ± 1.8 |
| 310 | 25.4 ± 6.0 | 310 | 8.9 ± 1.8 |
| 315 | 24.5 ± 5.8 | 315 | 8.3 ± 1.6 |
| 320 | 22.9 ± 5.3 | 320 | 7.4 ± 1.5 |
| 325 | 21.4 ± 4.9 | 325 | 6.6 ± 1.3 |
| 330 | 19.5 ± 4.4 | 330 | 5.9 ± 1.1 |
| 335 | 17.3 ± 3.7 | 335 | 5.1 ± .9 |
| 340 | 15.1 ± 3.1 | 340 | 4.5 ± .7 |
| 345 | 13.0 ± 2.6 | 345 | 3.9 ± .6 |
| 350 | 11.1 ± 2.1 | 350 | 3.4 ± .4 |
| 355 | 9.5 ± 1.7 | 355 | 3.1 ± .4 |
| 360 | 8.2 ± 1.4 | 360 | 2.8 ± .4 |
| 365 | 7.0 ± 1.1 | 365 | 2.5 ± .2 |
| 370 | 6.1 ± .8 | 370 | 2.3 ± .2 |
| 375 | 5.3 ± .7 | 375 | 2.1 ± .2 |
| 380 | 4.6 ± .5 | 380 | 2.0 ± .1 |
| 385 | 4.0 ± .4 | 385 | 1.9 ± .1 |
| 390 | 3.6 ± .3 | 390 | 1.8 ± .1 |
| 395 | 3.3 ± .2 | 395 | 1.7 ± .1 |
| 400 | 3.1 ± .2 | 400 | 1.6 ± .1 |

The overall SPF values were as follows:

| % TiO$_2$ | SPF |
|---|---|
| 2.5 | 7.4 ± 0.5 |
| 10.0 | 21.0 ± 1.7 |

Again the results for the monochromatic protection factors show that there is some protection provided throughout the UVB and UVA region.

EXAMPLE 22

The 40% TiO$_2$ aqueous dispersion from example 3 was incorporated into an oil in water suncream formulation containing 10% TiO$_2$. The cream was made by heating phase A to 75° C. and heating phase B to 75° C. Phase B is added to phase A, then phase C is added. Cool to 40° C. and add phases D and E.

| PHASE | INGREDIENT | % BY WEIGHT OF |
|---|---|---|
| A | Deionised water | 35.95 |
| A | Thickener (Carbopol 940) (2% Solution) | 15.00 |
| A | Tetrasodium EDTA | 0.10 |
| A | Propylene glycol | 2.00 |
| A | Emulsifier (Monamate CPA-40) | 2.00 |
| B | Mineral oil 65/75 | 7.50 |
| B | Isopropyl Myristate | 5.00 |
| B | Stearic acid XXX | 3.00 |
| B | Solvent (Promulgen D) | 1.50 |
| B | Silicone oil (SF96-100) | 2.00 |
| C | Triethanolamine 99% | 0.75 |
| D | Preservative (Glydant) | 0.20 |

-continued

| PHASE | INGREDIENT | % BY WEIGHT OF |
|---|---|---|
| E | TiO₂ Dispersion (40%) | 25.00 |

This cream was tested for monochromatic protection factors and SPF as previously.

EXAMPLE 22, 10% TiO₂

| Wavelength nm | Monochromatic Protection Factor |
|---|---|
| 290 | 9.6 ± 1.1 |
| 295 | 9.4 ± 1.3 |
| 300 | 9.4 ± 1.2 |
| 305 | 9.3 ± 1.1 |
| 310 | 9.1 ± 1.1 |
| 315 | 8.3 ± 1.1 |
| 320 | 8.5 ± 1.0 |
| 325 | 8.0 ± .9 |
| 330 | 7.6 ± .8 |
| 335 | 7.1 ± .8 |
| 340 | 6.6 ± .7 |
| 345 | 6.1 ± .6 |
| 350 | 5.6 ± .5 |
| 355 | 5.1 ± .4 |
| 360 | 4.7 ± .4 |
| 365 | 4.3 ± .3 |
| 370 | 4.0 ± .2 |
| 375 | 3.6 ± .2 |
| 380 | 3.3 ± .2 |
| 385 | 3.0 ± .1 |
| 390 | 2.8 ± .1 |
| 395 | 2.6 ± .1 |
| 400 | 2.5 ± .1 |

The overall SPF value obtained was 8.4+ −0.4 and again there is protection throughout the UVB and UVA regions.

I claim:

1. An aqueous dispersion of titanium dioxide comprising water, particles of titanium dioxide having an acicular shape and a dispersing agent selected from the group consisting of polymers or copolymers of an acrylic acid or substituted acrylic acid and salts of said polymers or copolymers and said titanium dioxide being present in an amount to produce a solids content for the dispersion of from 20 to 60 percent by weight and having a size such that the dispersion is substantially transparent to visible light and has a maximum extinction coefficient (E(max)) in the ultra violet range of wavelengths of at least 30 liters per gm per cm.

2. An aqueous dispersion according to claim 1 in which the particles of said titanium dioxide have a ratio of the largest dimension to the shortest dimension within the range 8:1 to 2:1.

3. An aqueous dispersion according to claim 2 in which the largest dimension is within the range 0.01 to 0.15 micron.

4. An aqueous dispersion of titanium dioxide comprising water, particles of titanium dioxide having an acicular shape and having a ratio of the largest dimension to the shortest dimension within the range 8:1 to 2:1 and wherein the longest dimension is within the range 0.01 to 0.15 microns and a dispersing agent selected from the group consisting of polymers or copolymers of an acrylic acid or substituted acrylic acid and salts of said polymers or copolymers and said titanium dioxide being present in an amount to produce a solids content for the dispersion of from 20 to 60 percent by weight.

5. An aqueous dispersion according to claim 4 in which the maximum extinction coefficient (E(max)) at a wavelength of 308 nm is at least 30 liters per gram per cm.

6. An aqueous dispersion according to claim 1 in which the maximum extinction coefficient at a wavelength of 308 nm is 40 liters per gram per cm.

7. An aqueous dispersion according to claim 3 in which the largest dimension is 0.02 to 0.1 micron.

8. An aqueous dispersion according to claim 1 in which the solids content is from 25 to 50 per cent by weight.

9. An aqueous dispersion according to claim 1 in which at least 80% by weight of the particles of said titanium dioxide have a largest dimension within the range 0.01 to 0.15 micron.

10. An aqueous dispersion according to claim 1 in which the particles of titanium dioxide are coated with one or more hydrous oxides of a metal or of silicon.

11. An aqueous dispersion according to claim 10 in which the hydrous oxide is of aluminium, zirconium, zinc or titanium.

12. An aqueous dispersion according to claim 10 in which the particles of titanium dioxide are coated with an amount of hydrous oxide when expressed as oxide of from 1.0 to 30.0 weight per cent based on weight of titanium dioxide.

13. An aqueous dispersion according to claim 12 in which the amount of hydrous oxide is from 5.0 to 20.0 weight per cent as oxide on weight of titanium dioxide.

14. An aqueous dispersion according to claim 10 in which the particles of titanium dioxide are coated with a hydrous oxide of aluminium and of silicon in a weight ratio of $Al_2O_3:SiO_2$ of at least 1.5 and not greater than 4.5.

15. An aqueous dispersion according to claim 14 in which the weight ratio $Al_2O_3:SiO_2$ is from 2.0 to 3.5.

16. An aqueous dispersion according to claim 1 in which the dispersing agent is an alkali metal salt or ammonium salt of said polymer or copolymer.

17. An aqueous dispersion according to claim 1 in which the copolymer is a copolymer of an acrylic acid and a sulphonic acid derivative.

18. An aqueous dispersion according to claim 1 in which the dispersing agent is a substantially linear molecule having a molecular weight of from 1000 to 10,000.

19. An aqueous dispersion according to claim 1 in which the amount of the dispersing agent is from 5 to 35 per cent by weight of the titanium dioxide in the dispersion.

20. An aqueous dispersion according to claim 19 in which the amount is from 10 to 25 per cent by weight.

21. A method for the manufacture of an aqueous dispersion comprising milling in the presence of particulate grinding medium particulate titanium dioxide in water in the presence of a dispersing agent selected from the group consisting of polymers or copolymers of an acrylic acid or substituted acrylic acid and salts of said polymers or copolymers, said titanium dioxide having an acicular shape and is present in an amount sufficient to produce a solids content of from 20 to 60 percent by weight until the titanium dioxide is dispersed in said water to produce a product absorbent to ultraviolet light and substantially transparent to visible light.

22. A method according to claim 21 in which the particulate titanium dioxide is acicular in shape in which the ratio of the largest dimension to the shortest dimension is within the range 8:1 to 2:1 and the largest dimension is from 0.01 to 0.15 micron.

23. A method according to claim 21 in which the milling is effected in a mill having one or more agitators operating at a speed of from 500 r.p.m. to 6000 r.p.m.

24. A method according to claim 21 in which milling is effected with an agitator mill having an agitator operating at a tip speed of the agitator of up to 10 meters/sec.

25. An aqueous dispersion according to claim 4 in which the particles of titanium dioxide are coated with one or more hydrous oxides of a metal or of silicon.

26. An aqueous dispersion according to claim 25 in which the hydrous oxide is of aluminum, zirconium, zinc or titanium.

27. An aqueous dispersion according to claim 25 in which the particles of titanium dioxide are coated with an amount of hydrous oxide when expressed as oxide of from 1.0 to 30.0 weight percent based on weight of titanium dioxide.

28. An aqueous dispersion according to claim 27 in which the amount of hydrous oxide is from 5.0 to 20.0 weight percent as oxide on weight of titanium dioxide.

29. An aqueous dispersion according to claim 25 in which the particles of titanium dioxide are coated with a hydrous oxide of aluminum and of silicon in a weight ratio $Al_2O_3:SiO_2$ of at least 1.5 and not greater than 4.5.

30. An aqueous dispersion according to claim 29 in which the weight ratio $Al_2O_3:SiO_2$ is from 2.0 to 3.5.

31. An aqueous dispersion according to claim 4 in which the copolymer is a copolymer of an acrylic acid and a sulphonic acid derivative.

32. An aqueous dispersion according to claim 4 in which the dispersing agent is a substantially linear molecule having a molecular weight of from 1,000 to 10,000.

33. An aqueous dispersion according to claim 4 in which the amount of the dispersing agent is from 5 to 35 percent by weight of the titanium dioxide in the dispersion.

34. An aqueous dispersion according to claim 33 in which the amount is from 10 to 25 percent by weight.

* * * * *